United States Patent [19]

Fukao et al.

[11] Patent Number: 4,962,254

[45] Date of Patent: Oct. 9, 1990

[54] PROCESS FOR PREPARING ALKYL-SUBSTITUTED AROMATIC HYDROCARBONS

[75] Inventors: Masami Fukao, Shiga; Takuo Hibi, Toyonaka; Kiyoshi Ikimi, Otokuni; Gohfu Suzukamo, Ibaraki, all of Japan

[73] Assignee: Sumitomo Chemical Company, Limited, Osaka, Japan

[21] Appl. No.: 391,242

[22] Filed: Aug. 9, 1989

[30] Foreign Application Priority Data

Aug. 12, 1988 [JP] Japan .................. 63-202468
Aug. 12, 1988 [JP] Japan .................. 63-202469

[51] Int. Cl.$^5$ .................. C07C 15/067; C07C 2/68
[52] U.S. Cl. .................. 585/452; 585/453; 585/467
[58] Field of Search .................. 585/452, 453, 467

[56] References Cited

U.S. PATENT DOCUMENTS 2,769,850 11/1956 Closson et al. .................. 585/452
2,771,495 11/1956 Pines et al. .................. 585/453
2,780,660 2/1957 Field et al. .................. 585/452
4,511,748 4/1985 Kudoh et al. .
4,620,056 10/1986 Shimizu et al. .
4,711,873 12/1987 Suzukamo et al. .
4,822,764 4/1989 Suzukamo et al. .

FOREIGN PATENT DOCUMENTS 1053229A 8/1984 Japan .
1259535 8/1969 United Kingdom .
1269280 8/1969 United Kingdom .

OTHER PUBLICATIONS

"Carbanions Additions in the Reaction of Aromatic Hydrocarbons with Monoölefins" by Herman Pines and Victor Mark, Mar. 14, 1956, Vo. 78, pp. 4316–4322.
"Base-Catalyzed Reactions of Hydrocarbons and Related Compounds" by Herman Pines and Wayne M. Stalick, Academic Press, pp. 240–308, 1977.

Primary Examiner—W. J. Shine
Assistant Examiner—James Saba
Attorney, Agent, or Firm—Birch, Stewart, Kolasch & Birch

[57] ABSTRACT

An alkyl-substituted hydrocarbon is prepared by alkylating an alkyl aromatic hydrocarbon having at least one hydrogen atom at an alpha-position in a side chain with an olefin in the presence of a solid base which is obtainable by heating an alumina, an alkali metal hydroxide and an alkali metal hydride or an alumina containing at least 1.3% by weight of water and an alkali metal hydride in an inert gas atmosphere at a temperature of 200° to 800° C. as a catalyst.

28 Claims, No Drawings

PROCESS FOR PREPARING ALKYL-SUBSTITUTED AROMATIC HYDROCARBONS

BACKGROUND OF THE INVENTION

1. Field of the Invention

The present invention relates to a process for preparing an alkyl-substituted aromatic hydrocarbon. More particularly, the present invention relates to a process for preparing an alkyl-substituted aromatic hydrocarbon by reacting an alkyl aromatic hydrocarbon having at least one hydrogen atom at an alpha-position in said alkyl side chain with an olefin in the presence of a solid base which is prepared from an alumina, an alkali metal hydroxide and an alkali metal hydride or from water-containing alumina and an alkali metal hydride at a temperature in a specific range, whereby the alpha position is alkylated.

2. Description of the Related Art

The alkyl-substituted aromatic hydrocarbons are useful as intermediates in the production of fine chemicals such as agricultural chemicals, pharmaceuticals and other chemicals and prepared by reacting the aromatic hydrocarbon having the hydrogen atom at the alpha-position in the side chain with the olefin in the presence of a base catalyst.

As the preparation process of the alkyl-substituted aromatic hydrocarbon, there are known a process which Utilizes a catalyst comprising metal sodium and chlorotoluene and a process which utilizes a catalyst comprising metal sodium supported on potassium carbonate (cf. J. Am. Chem. Soc., 78, 4316 (1956), GB Patent No. 1269280 and Japanese Patent Kokai Publication No. 53229/1986).

However, the conventionally used catalysts have various drawbacks such as insufficient catalytic activities, a low yield of the alkyl-substituted hydrocarbon per a unit amount of the catalyst and troublesome separation of the catalysts from the product. Further, the conventional catalysts suffer from such problem that when they contact the oxygen and/or moisture in the air, they tend to lose their activities or they are ignited.

SUMMARY OF THE INVENTION

One object of the present invention is to provide a base catalyst which effectively catalyzes the reaction of the aromatic hydrocarbon having the hydrogen atom at the alpha-position in the side chain with the olefin, can be easily separated from the product after reaction.

Another object of the present invention is to provide a process for producing an alkyl-substituted hydrocarbon by reacting the alkyl aromatic hydrocarbon having the hydrogen atom at the alpha-position in the side chain with the olefin.

Accordingly, the present invention provides a process for preparing an alkyl-substituted hydrocarbon comprising alkylating an alkyl aromatic hydrocarbon having at least one hydrogen atom at an alpha-position in a side chain with an olefin in the presence of a solid base which is obtainable by heating an alumina, an alkali metal hydroxide and an alkali metal hydride or an alumina containing at least 1.3 % by weight of water and an alkali metal hydride in an inert gas atmosphere at a temperature of 200° to 800° C. as a catalyst.

DETAILED DESCRIPTION OF THE INVENTION

The process of the present invention is characterized in the use of the specific solid base as the catalyst, which solid base is prepared by heating the alumina, the alkali metal hydroxide and the alkali metal hydride at the specific temperature.

As the alumina, various types of aluminas except α-alumina are used. Preferred examples of the alumina are γ-alumina, χ-alumina, ρ-alumina and η-alumina. Among them, those having a relatively large surface area are preferred.

As the alkali metal hydride, a hydride of an alkali metal of Group I of the Periodic Table such as lithium, sodium, potassium and rubidium is used. They may be used as a mixture. Among them, sodium hydride, potassium hydride, or a mixture of them, particularly potassium hydride are preferred. The amount of the alkali metal hydride is generally from 2 to 15 % by weight based on the weight of the alumina.

As the alkali metal hydroxide, any of hydroxides of the above exemplified alkali metals may be used. Preferably, sodium hydroxide, potassium hydroxide and cecium hydroxide are used. Mixtures of two or more alkali metal hydroxides may be used. The amount of the alkali metal hydroxide is generally from 5 to 40 % by weight based on the weight of the alumina.

In the preparation of the solid base, preferably the alumina is treated with the alkali metal hydroxide, and then the resulting product is reacted with the alkali metal hydride in the inert gas atmosphere.

For example, the alumina is heated to a desired temperature and mixed with the alkali metal hydroxide. Thereafter, the alkali metal hydride is added to the resulting product and the mixture is further heated. Alternatively, the alumina is impregnated with an aqueous solution of the alkali metal hydroxide, and water in said solution is removed. Then, the dried product is heated to a desired temperature. Thereafter, the alkali metal hydride is added to the product and further heated.

As the inert gas, nitrogen, helium, argon and the like are used.

In the preparation of the solid base to be used in the process of the present invention, the reaction temperature is important. Usually, the reaction temperature is from 200° to 800° C. Preferably, the alumina and the alkali metal hydroxide are reacted in a temperature range of 250° to 700° C., more preferably in a temperature range of 260° to 480° C., and the alkali metal hydride is reacted in a temperature range of 200° to 450° C.

The reaction time varies with other reaction conditions such as the reaction temperature. The reaction of the alumina with the alkali metal hydroxide may be completed within 0.5 to 10 hours, and the treatment with the alkali metal hydride may be completed within 10 to 300 minutes.

By the above reactions, the solid base which has high catalytic activity, good flowability and handleability can be obtained.

When water-containing alumina containing at least 1.3 % by weight of water is used as the alumina, the solid base having the same catalytic performances as above can be prepared with using no alkali metal hydroxide. Namely, the solid base catalyst can be prepared by reacting the alumina containing at least 1.3 % by weight of water with the alkali metal hydride in the inert gas atmosphere at a temperature of 200° to 800° C.

Various types of water-containing aluminas except for α-alumina can be used.

Generally, alumina is produced by calcining aluminum hydroxide. According to the calcining temperature and time, alumina has various metastable states and a water content varies so that various type of alumina are produced. In the present invention, such alumina may be used. Preferably, water-containing alumina with a large surface area such as γ-alumina, χ-alumina, ρ-alumina and η-alumina are used.

The water content may be expressed by weight loss on heating in the heating step in which the alumina in its original state is converted to α-alumina which is considered to include no removable water. Usually, the water content of the water-containing alumina is 1.3 to 25 % by weight, preferably 2 to 10 % by weight.

The amount of alkali metal hydride used in this preparation method is generally from 0.5 to 2.5 time, preferably 0.5 to 2.0 time molar equivalents of water contained in the alumina.

Again, the reaction temperature is important in this preparation method of the catalyst. Usually, the reaction temperature is from 200° to 800° C, preferably from 250° to 700° C., more preferably from 260° to 480° C.

The reaction time varies with other reaction conditions such as the reaction temperature. The reaction of the alumina and the alkali metal hydride may be completed within 10 to 300 minutes.

By the above reaction, the solid base which has the same properties as that prepared from the alumina, the alkali metal hydroxide and the alkali metal hydride, such as high catalytic activity, good flowability and handleability can be obtained. This may be because a part of the alkali metal hydride reacts with the water contained in the alumina to form the corresponding alkali metal hydroxide and as the result, the alumina, the alkali metal hydroxide and the alkali metal react with each other.

In the process of the present invention, the aromatic hydrocarbon having the hydrogen atom at the alphaposition in the side chain is reacted with the olefin in the presence of the above described solid base as the catalyst.

As such aromatic hydrocarbon, not only monocyclic aromatic hydrocarbons but also condensed polycyclic aromatic hydrocarbons may be used. In the aromatic hydrocarbons, the side chains may be closed to form a ring. Specific examples of the aromatic hydrocarbon are toluene, ethylbenzene, isopropylbenzene (cumene), n-propylbenzene, n-butylbenzene, sec.-butylbenzene, isobutylbenzene, xylene, cymene, diisopropylbenzene, methylnaphthalene, tetrahydronaphthalene, indan and the like. Among them, toluene, ethylbenzene and isopropylbenzene are preferred.

As the olefin, those having 2 to 20 carbon atoms are usually used. The olefin may be straight or branched. The carbon-carbon double bond may be a terminal or internal double bond. Preferably, the olefin having the terminal double bond is used. Specific examples of the olefin are ethylene, propylene, 1-butene, 2-butene, isobutylene, 1-pentene, 2-pentene, 1-hexene, 2-hexene, 3-hexene, 1-heptene, 2-heptene, 3-heptene, octene, nonene, 3-methyl-1-butene, 2-methyl-2-butene, 3-methyl-1-pentene, 3methyl-2-pentene and the like. Among them, ethylene, propylene, 1-butene and 2-butene are preferred.

The alkylation reaction according to the present invention may be carried out batchwise or continuously with the use of a fluidized bed or a fix bed.

The reaction temperature for the alkylation is usually from 0° to 300° C., preferably from 10° to 200° C.

The reaction pressure is from atmospheric pressure to 200 kg/cm$^2$, preferably from 2 to 100 kg/cm$^2$.

The molar ratio of the olefin to the aromatic hydrocarbon is usually from 0.1 to 10, preferably from 0.2 to 5.

In the batchwise reaction, the amount of solid base catalyst to be used is from 0.01 to 20 % by weight, preferably from 0.2 to 5 % by weight based on the weight of the aromatic hydrocarbon. The reaction time is generally from 0.05 to 50 hours, preferably from 1 to 25 hours.

In the continuous reaction, the mixture of the aromatic hydrocarbon and the olefin in the above molar ratio is supplied at LHSV of 0.1 to 600 hr$^{-1}$, preferably 0.5 to 400 hr$^{-1}$.

According to the present invention, the alkyl-substituted hydrocarbon is effectively prepared in the presence of the solid base catalyst in a small amount under the mild conditions. Further, the catalyst to be used according to the present invention is easily handled and post-treated after the reaction.

PREFERRED EMBODIMENTS OF THE INVENTION

Practically and presently preferred embodiments of the present invention will be illustrated by following examples.

Preparation of Solid Bases

Solid Base A

An activated alumina of 42–200 mesh (NKHD-24, a trade name of Sumitomo Chemical Co., Ltd.) (26.5 g) was stirred in an atmosphere of nitrogen at 510° C. for one hour and cooled to 380° C. Then, potassium hydroxide (2.5 g) was added to the alumina and the mixture was stirred at 380° C. for 3 hours followed by cooling to 310° C.

To the mixture, potassium hydride (2.33 g) was added and the mixture was stirred at 310° C. for 0.2 hour followed by cooling to room temperature to obtain Solid Base A.

Solid Base B

In the same manner as in the preparation of Solid Base A but using 1.78 g of potassium hydride, Solid Base B was prepared.

Solid Base C

In the same manner as in the preparation of Solid Base A but adding potassium hydroxide at 550° C. and using 1.81 g of potassium hydride, Solid Base C was prepared.

Solid Base D

To a solution of potassium hydroxide (2.5 g) and water (50 g), the same activated alumina as used in the preparation of Solid Base A (26.5 g) was added. Then, the mixture was dried with removing water at 70° C. under reduced pressure while stirring to obtain a solid material.

The solid material was stirred in an atmosphere of nitrogen at 250° C. for 3 hours and heated to 310° C.

Then, potassium hydride (3.18 g) was added to the solid material and the mixture was stirred at the same temperature for 0.2 hour followed by cooling to room temperature to obtain Solid Base D (24.8 g).

Solid Base E

In the same manner as in the preparation of Solid Base D but stirring the solid material at 380° C. and using 3.15 g of potassium hydride, Solid Base E was prepared.

Solid Base F

In the same manner as in the preparation of Solid Base D but stirring the solid material at 550° C. and using 3.25 g of potassium hydride, Solid Base F was prepared.

Solid Base G

In the same manner as in the preparation of Solid Base D but stirring the solid material at 700° C. and using 3.15 g of potassium hydride, Solid Base G was prepared.

Solid Base H

In the same manner as in the preparation of Solid Base A but using 2.5 g of sodium hydroxide in place of potassium hydroxide and 2 g of potassium hydride, Solid Base H was prepared.

Solid Base I

The same manner as in the preparation of Solid Base A but using 2.5 g of sodium hydroxide in place of potassium hydride, Solid Base I was prepared.

Solid Base J

In the same activated alumina used in the preparation of Solid Base A (26.5 g) and potassium hydroxide (2.5 g) were ground and mixed and then placed in a crucible and heated at 1,200° C. for 3 hours in a muffle furnace. The mixture was cooled to 200° C. and further to room temperature in a desiccator in an atmosphere of nitrogen to obtain a fine powder.

The fine powder was heated to 310° C. Then, to the heated powder, sodium hydride (2.6 g) was added while stirring. The mixture was further stirred at 310° C. for 0.2 hour followed by cooling to room temperature to obtain Solid Base J.

Solid Base K

To 40–200 mesh activated alumina containing 3.6 % of water (21.7 g) in an atmosphere of nitrogen, potassium hydride (2.6 g) was added. The mixture was heated to 360° C. while stirring and further stirred at the same temperature for 0.2 hour followed by cooling to room temperature to obtain Solid Base K (23.9 g).

Solid Base L

In the same manner as in the preparation of Solid Base K but using 1.8 g of potassium hydride, Solid Base L was prepared.

Solid Base M

In the same manner as in the preparation of Solid Base K but using 1.55 g of potassium hydride, Solid Base M was prepared.

Solid Base N

In the same manner as in the preparation of Solid Base K but using 1.4 g of potassium hydride, Solid Base N was prepared.

Solid Base O

To the same water-containing alumina as used in the preparation of Solid Base K (21.7 g) heated at 360° C. in an atmosphere of nitrogen, potassium hydride (0.95 g) was added while stirring and the mixture was further stirred at the same temperature for 0.2 hour. Then, the mixture was heated to 700° C. and further stirred at the same temperature for 3 hours and cooled to 360° C. To the mixture, potassium hydride (0.95 g) was added and the mixture was stirred at 360° C. for 0.2 hour followed by cooling to room temperature to obtain Solid Base O.

Solid Base P

To the same water-containing alumina as used in the preparation of Solid Base K (21.7 g) heated at 290° C in an atmosphere of nitrogen, potassium hydride (0.89 g) was added while stirring and the mixture was further stirred at the same temperature for one hour. Then, the mixture was placed in a crucible and heated at 1,200° C. for 3 hours in a muffle furnace. The mixture was cooled to 200° C. and further to room temperature in a desiccator in an atmosphere of nitrogen.

After heating the mixture to 360° C. in an atmosphere of nitrogen, sodium hydride (1.02 g) was added and the mixture was stirred at 360° C. for 0.2 hour followed by cooling to room temperature to obtain Solid Base P.

EXAMPLE 1

In a 600 ml autoclave equipped with a magnetic stirrer, Solid Base A (0.45 g) and cumene (240 g) were charged under nitrogen, heated to 160° C. while stirring at 1,000 rpm and then reacted at the same temperature for 3 hours while supplying ethylene gas under pressure of 10 kg/cm$^2$G. to produce tert.-amylbenzene (hereinafter referred to as "TAB").

After the reaction, the autoclave was cooled, and the catalyst was filtered off. The reaction mixture was analyzed with gas chromatography. The results are shown in Table 1.

The selectivity of TAB is calculated according to the following equation:

$$\text{Selectivity (\%)} = \frac{\text{Amount of produced } TAB \text{ (mole)} \times 100}{\text{Total amount of all produced alkyl-substituted compounds (mole)}}$$

EXAMPLES 2-16 AND COMPARATIVE EXAMPLES 1-2

In the same manner as in Example 1 but carrying out the reaction under the conditions shown in Table 1, the alkylation was carried out. The results are shown in Table 1.

In Examples 1 through 16, the catalyst was still active at the end of the reaction and the alkylation could be further carried out by using the same catalyst.

TABLE 1

| Example No. | Solid Base (g) | Reaction Temp. (°C.) | Reaction time (hrs) | Conversion of cumene (%) | Selectivity of TAB (%) |
|---|---|---|---|---|---|
| 1 | A (0.45) | ↑ | 3.0 | 98.9 | 99.2 |

TABLE 1-continued

| Example No. | Solid Base (g) | Reaction Temp. (°C.) | Reaction time (hrs) | Conversion of cumene (%) | Selectivity of TAB (%) |
|---|---|---|---|---|---|
| 2 | B (0.51) | ↑ | ↑ | 95.7 | 99.1 |
| 3 | C (0.49) | ↑ | ↑ | 91.3 | 95.2 |
| 4 | D (0.49) | 160 | 1.5 | 99.4 | 99.6 |
| 5 | E (0.38) | ↑ | ↑ | 93.7 | 99.4 |
| 6 | F (0.40) | ↑ | ↑ | 91.5 | 99.3 |
| 7 | G (0.39) | ↑ | ↑ | 36.4 | 98.7 |
| 8 | H (0.41) | ↑ | 3.0 | 99.7 | 99.2 |
| 9 | I (1.26) | ↑ | ↑ | 32.0 | 95.5 |
| 10 | K (0.48) | ↑ | 1.5 | 97.8 | 97.6 |
| 11 | L (0.32) | ↑ | 3.0 | 83.9 | 99.4 |
| 12 | M (0.37) | ↑ | ↑ | 84.9 | 98.6 |
| 13 | N (0.42) | ↑ | ↑ | 63.5 | 99.4 |
| 14 | O (0.41) | ↑ | ↑ | 95.7 | 95.6 |
| 15 | A (0.32) | 100 | 1.5 | 98.7 | 99.7 |
| 16 | L (0.39) | ↑ | 3.0 | 99.8 | 99.2 |
| C. 1 | J (1.98) | 160 | ↑ | 5.7 | 98.9 |
| C. 2 | P (1.38) | ↑ | ↑ | 0.18 | 99.0 |
| C. 3 | Mixture (8.49) | ↑ | ↑ | 19.4 | 73.9 |

COMPARATIVE EXAMPLE 3

To a 200 ml autoclave equipped with a magnetic stirrer, anhydrous potassium carbonate which had been calcined at 400° C. for 2 hours in a nitrogen atmosphere (8.19 g), metal sodium (0.3 g) and cumene (26.7 g) were charged under nitrogen, heated to 190° C. while stirring at 1,000 rpm then stirred at the same temperature for 2 hours.

After cooling the autoclave, additional cumene (53.3 g) was added and the mixture was heated to 160° C. while stirring at 1,000 rpm and then reacted at the same temperature for 3 hours while supplying ethylene gas under pressure of 10 kg/cm²G.

After the reaction, the product was analyzed in the same manner as in Example 1. The results are also shown in Table 1.

EXAMPLE 17

In a 300 ml autoclave equipped with a magnetic stirrer, Solid Base A (0.99 g) and cumene (80 g) were charged under nitrogen and then liquid propylene (100 ml) was injected under pressure. The reaction was then carried out at 160° C. for 24 hours while stirring to produce 1,1,2-trimethylpropylbenzene (hereinafter referred to as "TMPB").

After the reaction, the autoclave was cooled, and the reaction mixture was analyzed in the same manner as in Example 1 to find that the conversion of cumene was 71.1 % and the selectivity of TMPB was 85.7 %.

The selectivity of TMPB is calculated according to the following equation:

$$\text{Selectivity (\%)} = \frac{\text{Amount of produced } TMPB \text{ (mole)} \times 100}{\text{Total amount of all produced alkyl-substituted compounds (mole)}}$$

EXAMPLE 18

In the same manner as in Example 18 but using Solid Base L in place of Solid Base A, the alkylation was carried out.

After the reaction, the autoclave was cooled, and the reaction mixture was analyzed in the same manner as in Example 1 to find that the conversion of cumene was 46.0 % and the selectivity of TMPB was 85.4 %.

In Examples 17 and 18, the catalyst was still active at the end of the reaction and the alkylation could be further carried out by using the same catalyst.

COMPARATIVE EXAMPLE 4

In a 200 ml autoclave equipped with a magnetic stirrer, anhydrous potassium carbonate which had been calcined at 400° C. for 2 hours in a nitrogen atmosphere (8.86 g), metal sodium (0.3 g) and cumene (81.2 g) were charged under nitrogen, heated to 190° C. while stirring and then stirred at the same temperature for 2 hours.

After cooling the autoclave, liquid propylene (70 ml) was injected under pressure and the mixture was stirred at 160° C. for 24 hours.

After the reaction, the product was analyzed in the same manner as in Example 1 to find that the conversion of cumene was 8.0 % and the selectivity of TMPB was 81.5 %.

EXAMPLE 19

In a 300 ml autoclave equipped with a magnetic stirrer, Solid Base A (2.81 g) and toluene (80 g) were charged under nitrogen and then liquid propylene (70 ml) was injected under pressure. The reaction was carried out at 160° C. for 6 hours while stirring to produce isobutylbenzene (hereinafter referred to as "IBB").

After the reaction, the product was analyzed in the same manner as in Example 1 to find that the conversion of toluene was 22.9 % and the selectivity of IBB was 91.0 %. The selectivity of IBB was calculated according to the following equation:

$$\text{Selectivity (\%)} = \frac{\text{Amount of produced } IBB \text{ (mole)} \times 100}{\text{Total amount of all produced alkyl-substituted compounds (mole)}}$$

EXAMPLE 20

In the same manner as in Example 20 but using Solid Base K in place of Solid Base A, the alkylation was carried out.

After the reaction, the product was analyzed in the same manner as in Example 1 to find that the conversion of toluene was 21.2 % and the selectivity of IBB was 91.5 %.

In Examples 19 and 20, the catalyst was still active at the end of the reaction and the alkylation could be further carried out by using the same catalyst.

COMPARATIVE EXAMPLE 5

In a 200 ml autoclave equipped with a magnetic stirrer, anhydrous potassium carbonate which had been calcined at 400° C. for 2 hours in a nitrogen atmosphere (8.45 g), metal sodium (0.3 g) and toluene (26.6 g) were charged under nitrogen, heated to 190° C. while stirring at 1,000 rpm and then stirred at the same temperature for 2 hours.

After cooling the autoclave, additional toluene (53.2 g) was added and liquid propylene (70 ml) was injected under pressure. Then the mixture was stirred at 160° C. for 6 hours.

After the reaction, the product was analyzed in the same manner as in Example 1 to find that the conversion of toluene was 3.5 % and the selectivity of IBB was 88.2 %.

What is claimed is:

1. A process for preparing an alkyl-substituted hydrocarbon comprising alkylating an alkyl aromatic hydrocarbon having at least one hydrogen atom at an alpha-position in a side chain with an olefin in the presence of a solid base which is obtainable by reacting an alumina, an alkali metal hydroxide and an alkali metal hydride or an alumina containing at least 1.3 % by weight of water and an alkali metal hydride in an inert gas atmosphere at a temperature of 200° to 800° C. as a catalyst.

2. The process according to claim 1, wherein the solid base is one which is obtainable by reacting the alumina, the alkali metal hydroxide and the alkali metal hydride.

3. The process according to claim 2, wherein the alkali metal hydroxide is reacted at a temperature of 250° to 700° C.

4. The process according to claim 3, wherein the alkali metal hydroxide is reacted at a temperature of 260° to 480° C.

5. The process according to claim 2, wherein the alkali metal hydroxide is at least one selected from the group consisting of sodium hydroxide and potassium hydroxide.

6. The process according to claim 2, wherein the amount of the alkali metal hydroxide is 5 to 40 % by weight based on the weight of the alumina.

7. The process according to claim 2, wherein the alkali metal hydride is reacted at a temperature of 200° to 450° C.

8. The process according to claim 2, wherein the alkali metal hydride is at least one selected from the group consisting of sodium hydride and potassium hydride.

9. The process according to claim 8, wherein the alkali metal hydride is potassium hydride.

10. The process according to claim 2, wherein the amount of the alkali metal hydride is 2 to 15 % by weight based on the weight of the alumina.

11. The process according to claim 1, wherein the aromatic hydrocarbon having the hydrogen atom at the alphaposition in the side chain has 1 to 10 carbon atoms in the side chain.

12. The process according to claim 11, wherein the aromatic hydrocarbon is at least one selected from the group consisting of toluene, ethylbenzene, isopropylbenzene and diisopropylbenzene.

13. The process according to claim 1, wherein the olefin has 2 to 20 carbon atoms.

14. The process according to claim 13, wherein the olefin is selected from the group consisting of ethylene and propylene.

15. The process according to claim 1, wherein the alkylation temperature is from 10° to 200° C.

16. The process according to claim 1, wherein the solid base is one which is obtainable by reacting the watercontaining alumina and the alkali metal hydride.

17. The process according to claim 16, wherein the reaction of the water-containing alumina and the alkali metal hydride is carried out at a temperature of 250° to 700° C.

18. The process according to claim 16, wherein the reaction of the water-containing alumina and the alkali metal hydride is carried out at a temperature of 260° to 480° C.

19. The process according to claim 16, wherein the alkali metal hydride is at least one selected from the group consisting of sodium hydride and potassium hydride.

20. The process according to claim 19, wherein the alkali metal hydride is potassium hydride.

21. The process according to claim 16, wherein the amount of the alkali metal hydride is 0.5 to 2.5 time molar equivalents of water contained in the alumina.

22. The process according to claim 21, wherein the water content in the alumina is from 1.3 to 25 % by weight.

23. The process according to claim 22, wherein the water content in the alumina is from 2 to 10 % by weight.

24. The process according to claim 16, wherein the aromatic hydrocarbon having the hydrogen atom at the alphaposition position in the side chain has 1 to 10 carbon atoms in the side chain.

25. The process according to claim 24, wherein the aromatic hydrocarbon is at least one selected from the group consisting of toluene, ethylbenzene, isopropylbenzene and diisopropylbenzene.

26. The process according to claim 16, wherein the olefin has 2 to 20 carbon atoms.

27. The process according to claim 26, wherein the olefin is selected from the group consisting of ethylene and propylene.

28. The process according to claim 16, wherein the alkylation temperature is from 10° to 200° C.

* * * * *